United States Patent [19]

Mohanty et al.

[11] Patent Number: 5,777,889
[45] Date of Patent: Jul. 7, 1998

[54] METHOD AND APPARATUS FOR EVALUATING MOLECULAR STRUCTURES USING RELATIVISTIC INTEGRAL EQUATIONS

[75] Inventors: Ajaya Kumar Mohanty, Red Hook, N.Y.; Surya Narayan Panigrahy, Woodridge, Ill.

[73] Assignee: International Business Machines Corporation, Armonk, N.Y.

[21] Appl. No.: 310,460

[22] Filed: Sep. 22, 1994

[51] Int. Cl.$^6$ ............................................. G06F 19/00
[52] U.S. Cl. ................................. 364/499; 364/578
[58] Field of Search ............................ 364/188, 189, 364/400, 496–499, 524, 527, 550, 551.01, 735, 578, 500; 436/8; 434/278, 279, 280; 935/87

[56] References Cited

U.S. PATENT DOCUMENTS

| | | | |
|---|---|---|---|
| 4,660,151 | 4/1987 | Chipman et al. | 364/498 |
| 4,719,582 | 1/1988 | Ishida et al. | 364/498 |
| 4,855,931 | 8/1989 | Saunders | 364/499 |
| 4,987,548 | 1/1991 | Saito et al. | 364/498 |
| 5,420,805 | 5/1995 | Still et al. | 364/497 X |
| 5,424,963 | 6/1995 | Turner et al. | 364/499 X |

OTHER PUBLICATIONS

"A Dirac–Fock Self–Consistent Field Method for Closed–Shell Molecules Including Breit Interaction", A. K. Mohanty, International Journal of Quantum Chemistry, vol. 42, pp. 627–662 (1992).

*Primary Examiner*—Joseph Ruggiero
*Attorney, Agent, or Firm*—Floyd A. Gonzalez; Michaelson & Wallace

[57] ABSTRACT

An improved method of evaluating molecular structures using relativistic integral equations. The method transforms Cartesian non-relativistic integrals into relativistic integrals using a two-step process. A first step transforms two indecises of the non-relativistic integral equations into a plurality of intermediate equations. A second step transforms the plurality of intermediate set of integrals into relativistic integral. The relativistic integrals are then used to evaluate the relativistic behavior of the molecular structure.

14 Claims, 3 Drawing Sheets

METHOD AND APPARATUS FOR EVALUATING MOLECULAR STRUCTURES USING RELATIVISTIC INTEGRAL EQUATIONS

BACKGROUND OF THE DISCLOSURE

1. Field of the Invention

The invention relates to methods for evaluating molecular structures and particularly, to methods of evaluating primitive integrals in molecular structures using relativistic equations.

2. Description of the Prior Art

Typically, molecular structures are mathematically modeled using non-relativistic Shrodinger wave equations, i.e., equations that do not take into account relativistic effects upon electrons within the molecular structure. Generally, each electron in a particular atom is modeled by a wave function, e.g., obtained by solving conventional Shrodinger wave equation. The wave functions for all the electrons in the atom form a set of integral equations. Individual atomic models are then combined in a conventional manner to achieve a non-relativistic model of a particular molecular structure.

In a non-relativistic model of a molecular structure the wave function of the electron uses a set of N-basis eigenfunctions, where N is an integer value. The basis eigenfunctions define a matrix of eigenvalues that can be numerically evaluated using a computer. Typically, such computation requires $N^4$ computational operations to reach a solution; where N, for a relatively small molecule, can be a few hundred.

Non-relativistic models are sufficiently accurate for analyzing molecular structures containing relatively light atoms, e.g., hydrogen, helium and the like. Such models are used to accurately predict the interaction of various atoms with other atoms or molecules. As such, scientists can research certain reactions between molecules and atoms using a computer rather than laboratory apparatus. However, for heavier atoms, such as palladium, platinum, gold and the like, the inner-most electrons of these atoms have velocities which nearly approach the speed of light. As such, effects of relativity significantly alter the behavior of the interaction of these electrons with other electrons in the molecular structure. Consequently, non-relativistic models do not accurately model molecular structures containing heavy atoms.

To achieve modeling of molecular structures containing heavy atoms, physicists have developed relativistic models of atoms and molecules based on Dirac-Coulomb-Breit-Hamiltonian. Such models typically utilize kinetically balanced, Guassian-type relativistic basis functions that are directly transformed from the non-relativistic Cartesian basis functions. The relativistic integrals are then obtained by transforming the integrals over the Cartesian basis to the corresponding relativistic basis using the matrix of transformation. However, such transformations alone typically require $N^5$ computational operations to attain the relativistic basis functions; where N is an integer value that can be as large as one thousand. As such, using relativistic methods to model structures containing heavy atoms typically requires the use of a supercomputer to complete the transformation within a reasonable amount of time.

Thus, a need exists in the art for an efficient method of transforming non-relativistic Cartesian equation sets (integrals) into relativistic equation sets (integrals) to facilitate relativistic modeling of a molecular structure. Additionally, such a transformation should be accomplished using a minimum number of computational operations.

SUMMARY OF THE INVENTION

Our invention overcomes certain disadvantages heretofore associated with evaluating molecular structures using relativistic integrals. Specifically, to overcome these disadvantages, our invention provides a method of facilitating analysis of these structures by transforming non-relativistic integral equations into relativistic integral equations using a minimal number of computational operations. Consequently, the relativistic integral equations can be numerically solved to facilitate modeling of an atomic or molecular structure.

In general, our inventive technique transforms conventional, non-relativistic integrals into relativistic integrals. The resultant relativistic integrals take advantage of certain mathematical symmetries to decrease the number of computational steps typically associated with transforming and numerically solving non-relativistic and relativistic integral equations.

Specifically, our invention transforms a plurality of Cartesian non-relativistic integrals that define properties of an atomic structure of a molecule or atom into a plurality of intermediate equations. These intermediate equations are then transformed into a plurality of relativistic integrals defining relativistic properties of structure of the molecule or atom. Each step of our inventive method provides a two-index transformation of the integrals. By taking advantage of certain symmetries within the relativistic integrals, our inventive two-step transformation process significantly reduces the number of numerical operations from the number of numerical operations that are necessary to perform a four-index transformation in a single step.

Once the relativistic integrals are determined, a conventional Dirac-Hartree-Fock technique is used to find numerical solutions to a set of non-linear equations. These solutions are then used to explore properties of the molecular structure such as potential energy and bond length between atoms within the structure.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION OF THE PREFERRED EMBODIMENT

In general, our invention is a method for transforming non-relativistic Cartesian integrals into relativistic integrals which are used to facilitate evaluation of molecular structures. The resultant relativistic equations enable scientists to study molecular structures containing so-called "heavy"

atoms, e.g., palladium, gold, silver and the like. Because the inner-most electrons of these heavy atoms have velocities that are near the speed of light, molecular structures containing these atoms can only be accurately modeled and evaluated using relativistic equations.

Figure 1:
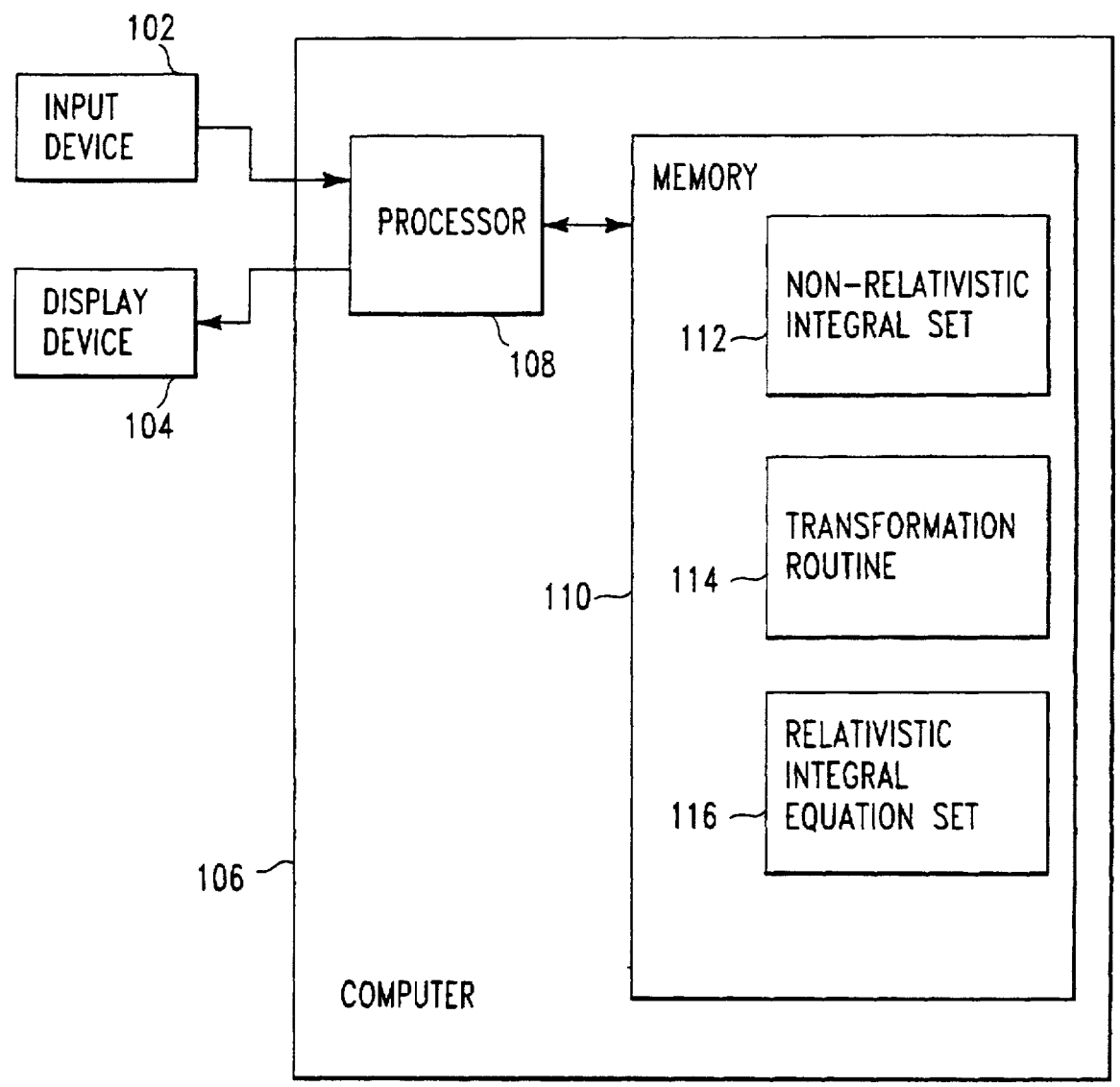
FIG. 1 depicts a high-level block diagram of a computer system used to implement our inventive method of evaluating molecular structures represented by two-electron repulsion integrals.

FIG. 1 depicts a high-level block diagram of computer system 100 used to implement our inventive method. The computer system contains conventional input device 102, conventional display device 104 and computer 106. The computer contains processor 108 and memory 110. The computer can be one of many computers currently available to consumers. Illustratively, computer 106 is a model 3090 manufactured by International Business Machines Corporation of Armonk, N.Y.

Our inventive method is illustratively implemented in software and stored in memory 110. Our invention lies in transformation routine 114. In operation, transformation routine 114 transforms pre-generated, non-relativistic integral set 112 into relativistic integral equation set 116. Typically, the non-relativistic equation set is a set of electron repulsion integrals (ERIs) which are defined by any one of the many conventional non-relativistic models such as the Hartree-Fock model.

Figure 2:
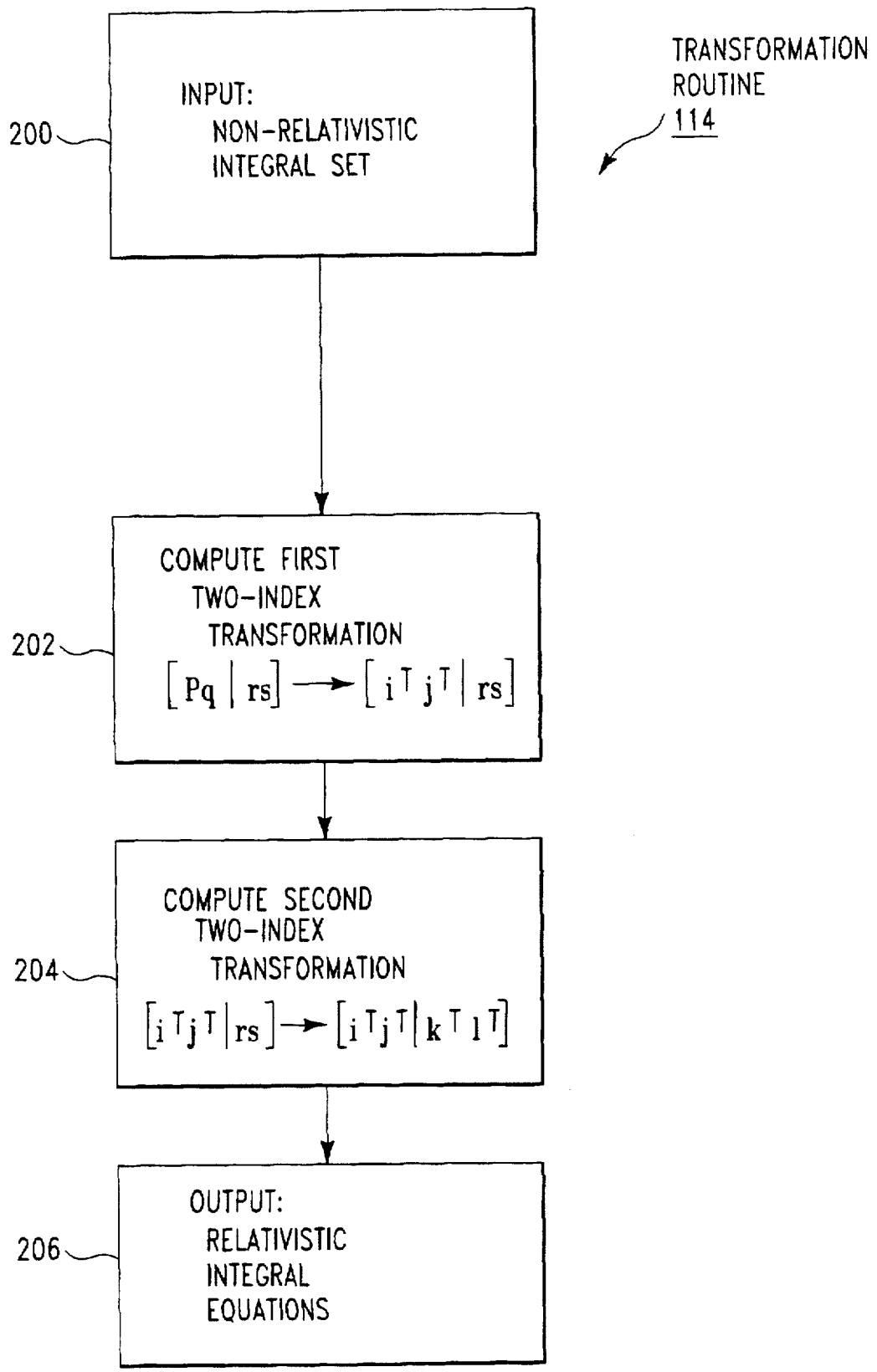
FIG. 2 depicts a high-level flow chart of our inventive method.

FIG. 2 depicts a high-level flow chart of transformation routine 114. To best understand the operation of routine 114, prior to specifically discussing this routine, we will first discuss the underlying theory and mathematics supporting our invention.

Within the context of the well-known Dirac-Hartree-Fock theory for describing relativistic effects, each electron is described by four components of a relativistic symmetry spinor. As such, let $\psi$ be represented by four matrix components: $\psi_1$, $\psi_2$, $\psi_3$ and $\psi_4$. Using well-known terminology, $\psi_1$ and $\psi_2$ can be represented as a two-component matrix: $\psi_{LARGE}$ or $\psi_L$. Similarly, $\psi_3$ and $\psi_4$ can be represented as a two-component matrix: $\psi_{SMALL}$ or $\psi_S$. As is well-known, the ratio of $\psi_L$ to $\psi_S$ roughly equals the speed of light.

Furthermore, let $\Gamma^{L\pm(1)}$ and $\Gamma^{L\pm(0)}$, $\Gamma^{S\pm(1)}$ and $\Gamma^{S\pm(0)}$ denote two-component spinor matrices which transform a conventional non-relativistic two-electron repulsion integral having a Cartesian basis type into relativistic integrals of the type $J^{T_i}{}_{Ap}J^{T_j}{}_{Bq}J^{T_k}{}_{Cr}J^{T_l}{}_{Ds}$. Indices i,j,k, and l have both positive and negative values indicating a direction of spin, up is positive and down is negative, for an electron. The specific value of i,j,k, and l depends on the sign of the respective $\kappa$ values, where:

$$\kappa = -2\left(j + \frac{1}{2}\right)(j-l)$$

where: j=a total angular momentum quantum number, and l=an orbital quantum number. Additionally, T and T' can be either L (large) or S (small). Consequently, the combined transformation matrices $\Gamma^{L(1)}$ and $\Gamma^{L(0)}$ are constructed from $\Gamma^{L\pm(1)}$ and $\Gamma^{L\pm(0)}$ as $$\Gamma^{T(1)} = \Gamma^{T+(1)} + \Gamma^{T-}, \qquad (1)\text{ and}$$

$$\Gamma^{T(0)} = \Gamma^{S+(0)} + \Gamma^{T-(0)}, \qquad (2)$$

where matrices $\Gamma^{T(1)}$ and $\Gamma^{T(0)}$, denote the upper and lower matrix components of $\Gamma^T$, respectively.

Let us denote, using the well-known bracket notation of Dirac, the two-electron repulsion integrals over a set of Cartesian basis functions $\{X_P\}$ as, $$[pq|rs] = [rq|r_{12}^{-1}|rs] = \int d\vec{r}_1 d\vec{r}_2 (\phi_p(r_1)\phi_q(r_1)r_{12}^{-1}\phi_r(r_2)\phi_s(r_2)). \qquad (3)$$

Where:

$r_{12}^{-1}$ is the Coulomb repulsion operator;

$\vec{r}_1$ and $\vec{r}_2$ are the respective locations of the two electrons;

$\phi$ is the basis function for each index p,q,r and s; and

[pq|rs] is the conventional charge cloud (bracket) notation for the two-electron repulsion integral.

A conventional four-index transformation of equation (3) over relativistic spinor functions $(\chi_L)$ that correspond to the non-relativistic two-electron repulsion integral in Equation (3) can be written as $$[i^{T_j}jk^Tl^{T'}] = \sum_{p=1}^{N}\sum_{q=1}^{N}\sum_{r=1}^{N}\sum_{s=1}^{N} \{\Gamma_{ip}^{T(1)\dagger}\Gamma_{kr}^{T(1)\dagger}[pq|rs]\Gamma_{qj}^{T(1)}\Gamma_{sl}^{T(1)} + \qquad (4)$$
$$\Gamma_{ip}^{T(0)\dagger}\Gamma_{kr}^{T(0)\dagger}[pq|rs]\Gamma_{qj}^{T(0)}\Gamma_{sl}^{T(0)}\}$$

where N represents the total number of Cartesian basis functions. To directly implement Equation (4) and solve this equation using a computer requires $N^8$ numerical operations. Typically, such a solution for heavy atoms requires a significant amount of computing time.

Alternatively, using our invention, the number of computational operations to solve Equation (4) is significantly reduced. Typically, the four-index transformation of Equation (4) is achieved using two sequential two-index transformations as shown in Equations (5) and (6).

$$[i^{T_j}j|rs] = \sum_{p=1}^{N}\sum_{q=1}^{N} \{\Gamma_{ip}^{T(1)\dagger}[pq|rs]\Gamma_{qj}^{T(1)} + \Gamma_{ip}^{T(0)\dagger}[pq|rs]\Gamma_{qj}^{T(0)}\} \qquad (5)$$

$$[i^{T_j}jk^Tl^{T'}] = \sum_{p=1}^{N}\sum_{q=1}^{N} \{\Gamma_{kr}^{T(1)\dagger}[ij|rs]\Gamma_{sl}^{T(1)} + \Gamma_{kr}^{T(0)\dagger}[ij|rs]\Gamma_{sl}^{T(0)}\} \qquad (6)$$

The two-index transformation represented by Equation (5) involves $N^2$ computational operations and Equation (6) requires $2N^3$ operations; hence, the full four-index transformation involves approximately $N^5$ computation operations. Typically, such a procedure requires many less computational operations to perform a complete four-index transformation than previously required by directly solving Equation (4).

The explicit transformation which results in each of the relativistic integrals of type $J^{LL;LL}$, $J^{LL;SS}$, and $J^{SS;SS}$ using the transformation matrices $\Gamma^{L(1)}$, $\Gamma^{L(0)}$, $\Gamma^{S(1)}$, $\Gamma^{S(0)}$ are given in the following equations. The transformation that results in $J^{LL;LL}{}_{Ai,Bj,Ck,Dl}$ is:

$$J^{LL;LL}_{Ai,Bj,Ck,Dl} = \sum_{r,s}^{N} \{\Gamma_{kr}^{L(1)\dagger}[ij|rs]\Gamma_{sl}^{L(1)} + \Gamma_{kr}^{L(0)\dagger}[ij|rs]\Gamma_{sl}^{L(0)}\} \qquad (7a)$$

where:

$$[ij|rs] = \sum_{p,q}^{N} \{\Gamma_{ip}^{L(1)\dagger}[pq|rs]\Gamma_{qj}^{L(1)} + \Gamma_{ip}^{L(0)\dagger}[pq|rs]\Gamma_{qj}^{L(0)}\} \qquad (7b)$$

The transformation that results in $J^{LL;SS}{}_{Ai,Bj,Ck,Dl}$ is:

$$J^{LL;SS}_{Ao,Bk,Cl,Dl} = \sum_{r,s}^{N} \{\Gamma_{kr}^{L(1)\dagger}[ij|rs]\Gamma_{sl}^{L(1)} + \Gamma_{kr}^{L(0)\dagger}[ij|rs]\Gamma_{sl}^{L(0)}\} \qquad (8a)$$

where:

$$[ij|rs] = \sum_{p,q}^{N} \{\Gamma_{ip}^{S(1)\dagger}[pq|rs]\Gamma_{qj}^{S(1)} + \Gamma_{ip}^{S(0)\dagger}[pq|rs]\Gamma_{qj}^{S(0)}\} \qquad (8b)$$

The transformation that results in $J^{SS,SS}_{Ai,Bj,Ck,Dl}$ is:

$$J^{SS,SS}_{Ai,Bj,Ck,Dl} = \sum_{r,s}^{N} \{\Gamma^{S(1)\dagger}_{kr}|ijlrs|\Gamma^{S(1)}_{sl} + \Gamma^{S(0)\dagger}_{kr}|ijlrs|\Gamma^{S(0)}_{sl}\} \quad (9a)$$

where:

$$|ijlrs| = \sum_{p,q}^{N} \{\Gamma^{S(1)\dagger}_{ip}|pqlrs|\Gamma^{S(1)}_{qj} + \Gamma^{S(0)\dagger}_{ip}|pqlrs|\Gamma^{S(0)}_{qj}\} \quad (9b)$$

Since the Coulomb repulsion operator is symmetric in two-particle electronic coordinate space, the two-electron repulsion integrals have certain permutation symmetries depending on the nature of one-electron orbitals. Recognizing and utilizing these symmetries reduces the number of computation operations necessary to perform the transformations set forth above. For example, if the one-electron orbitals are real, as they are in the Cartesian basis, there are seven symmetries in the electron repulsion integrals, viz., $$|pqlrs|=|qplrs|=|qplsr|=|rslpq|=|srlpq|=|rslqp|=|srlqp| \quad (10)$$

However, the number of symmetries is reduced to 4 if the one-electron orbitals are complex. The symmetries are given as $$|ijlkl|=|kllij|=|jillk|^{\dagger}=|lklji|^{\dagger} \quad (11)$$

The symmetry described in Equation (11) has been incorporated in the two-step transformation process defined by Equations (7a)–(9b).

For efficient memory management while processing the resulting relativistic integral equations in a computer, it is best to transform the non-relativistic integrals to a relativistic basis which share the same exponents for a given spinor function quartet, i.e., s,p,d, and f spinor function. For example, one can represent an s,p,d,f-type spinor function as $20^4$ Cartesian (non-relativistic) integrals. When these Cartesian integrals are transformed into relativistic integrals representing $s_{1/2}$, $P_{1/2}$,$P_{3/2}$,$d_{3/2}$,$d_{5/2}$-type spinor functions with both positive and negative quantum numbers there are only $18^4$ integrals to evaluate. Thus, by using the same exponents, the number of relativistic integrals to be numerically evaluated is further reduced.

Furthermore, it is advantageous to transform the Cartesian integral to relativistic integrals for $J^{LLLL}$, $J^{LLSS}$, and $J^{SSSS}$ simultaneously, i.e., by storing and re-using the intermediate results from solving Equation (5).

Returning now to FIG. 2, in step 200, the input integral set, i.e., Equation (3), is supplied to transformation routine 114. Generally, this non-relativistic Cartesian integral set is evaluated by standard techniques.

At step 202, each Cartesian integral [pqlrs] is partially transformed into intermediate equations [ijlrs] using Equation (5). In particular, when the general transformation matrices $\Gamma^{T(0)}$ are appropriately replaced with the relativistic transformation matrices $\Gamma^{S(0)}$ or $\Gamma^{L(0)}$, a subroutine executed at step 204 solves Equations (7b), (8b) and (9b), i.e., performs the first two-index transformation equations. As discussed above, the result of these transformations are generally represented by an intermediate set of integrals [ijlrs]. Subsequently, at step 204, these intermediate integrals are operated upon by Equations (7a), (8a) and (9a). Equations (7a), (8a) and (9a) are a second two-index transformation shown in general form as Equation (6). The results from Equations (7a), (8a) and (9a) are generally represented as relativistic integral integrals [ijlkl], and particularly, represented as the specific relativistic integrals $J^{LLLL}$, $J^{LLSS}$, and $J^{SSSS}$. Thus, transformation routine 114 generates, at step 206, an output containing the relativistic integral equations.

A typical system in which the transformation routine would find use is in a system for evaluating catalytic reactions that involve relatively heavy atoms such as palladium or platinum. Our inventive transformation is particularly useful for evaluating heavy atoms and molecular structures containing such atoms, since, as is well-known in the art, non-relativistic models of heavy atoms are generally inaccurate.

Figure 3:
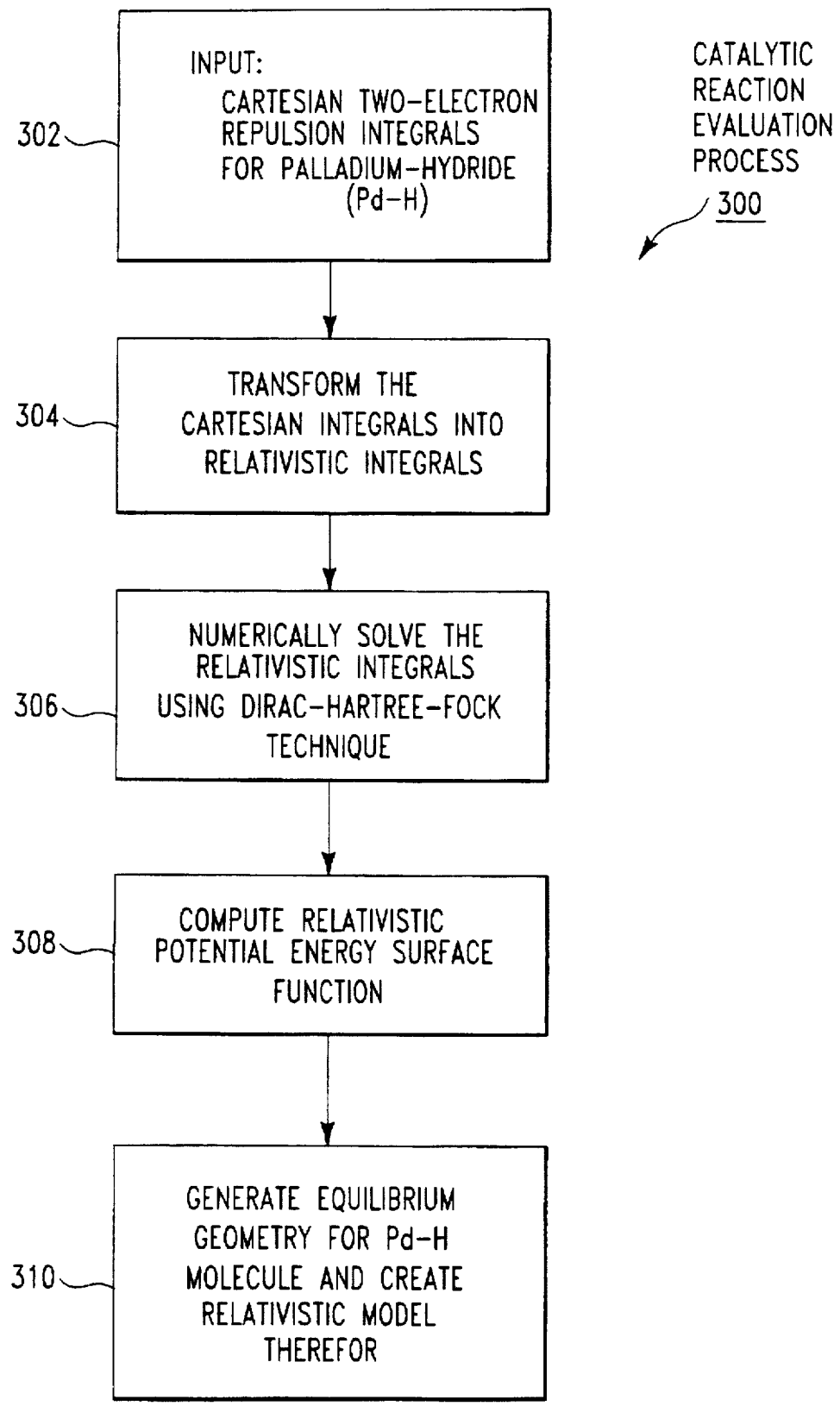
FIG. 3 depicts an illustrative application of our inventive method using a catalytic reaction evaluation process.

FIG. 3 depicts illustrative process 300 for facilitating this particular application in the evaluation of catalytic reactions. At step 302, a user of the system enters a set of Cartesian two-electron repulsion integrals (non-relativistic) for a molecule to be studied, e.g., palladium-hydride (Pd-H). Typically, such integrals would be recalled from a database of integrals containing integrals that represent various molecules and elements in a periodic table. These integrals would be generated through standard non-relativistic programs.

At step 304, each non-relativistic integral is transformed, using the transformation method discussed above and depicted in FIG. 2, into a relativistic integral. In this manner, our invention generates a set of relativistic integrals.

At step 306, a numerical solution for the relativistic molecular structure is produced using a conventional Dirac-Hartree-Fock technique. From the solution to the relativistic integrals, a relativistic potential energy surface function is conventionally generated. This surface function is analyzed to find a particular reaction between the palladium and hydrogen atoms at which a minimum potential energy occurs.

This particular bond length is conventionally used in step 310 to find the equilibrium geometry for the palladium-hydride molecule, and ultimately, facilitate geometric modeling of the molecule. Our full four-component method can be used to calibrate the approximate methods.

From the foregoing discussion, those skilled in the art will realize the impact of our invention in facilitating the evaluation of many aspects of molecular structures. The example of determining the bond length of a palladium-hydride molecule is only one illustrative use of our invention.

Although a single embodiment which incorporates that teachings of the present invention has been shown and described in detail herein, those skilled in the art can readily devise many other varied embodiments that still incorporate these teachings.

We claim:

1. A method of generating and displaying a relativistic physical description of a predetermined molecular structure using a computer system containing a memory, a processor, an input device and a display device, said predetermined molecular structure containing heavy elements having relativistic features, said method comprising the steps of:

inputting to said computer system a non-relativistic physical description of said predetermined molecular structure;

storing within said memory, in response to said inputting step, a first data set comprising non-relativistic, Cartesian, two-electron repulsion integrals functionally related to said non-relativistic physical description of said predetermined molecular structure;

transforming said first data set into a second data set, said second data set comprising relativistic integrals functionally related to said non-relativistic physical description of said predetermined molecular structure;

numerically solving said relativistic integrals to generate relativistic numerical parameters of said predetermined molecular structure;

evaluating said relativistic numerical parameters and said non-relativistic physical description;

generating, in response to said evaluating step, said relativistic physical description of said predetermined molecular structure, said relativistic physical description including at least one of said relativistic features of said predetermined molecular structure; and displaying said relativistic physical description, including said at least one of said relativistic features, of said predetermined molecular structure on said display device.

2. The method of claim 1 wherein said transforming step includes transforming said first data set into an intermediate data set comprising intermediate integrals functionally related to said non-relativistic, Cartesian, two-electron repulsion integrals, and transforming said intermediate data set into said second data set.

3. The method of claim 2 wherein the step of said transforming said first data set into an intermediate data set comprises evaluating the following expression:

$$[i^T j^T |rs] = \sum_{p=1}^{N} \sum_{q=1}^{N} \{\Gamma_{ip}^{T(1)\dagger}[pq|rs]\Gamma_{qj}^{T(1)} + \Gamma_{ip}^{T(0)\dagger}[pq|rs]\Gamma_{qj}^{T(0)}\}$$

where:

[pq|rs] is a bracket notation representing the plurality of two-electron repulsion integrals;

$[i^T j^T |rs]$ represents the plurality of intermediate set of integrals;

$\Gamma_{ip}^{T(1)\dagger}$, $\Gamma_{qj}^{T(1)}$, $\Gamma_{ip}^{T(0)\dagger}$, and $\Gamma_{qj}^{T(0)}$ each represent transformation matrices; and N represents a number of Cartesian basis functions.

4. The method of claim 3 wherein the step of said transforming said intermediate data set into said second data set comprises evaluating the following expression:

$$[i^T j^T |k^T l^T] = \sum_{p=1}^{N} \sum_{q=1}^{N} \{\Gamma_{kr}^{T(1)\dagger}[ij|rs]\Gamma_{sl}^{T(1)} + \Gamma_{kr}^{T(0)\dagger}[ij|rs]\Gamma_{sl}^{T(0)}\}$$

where:

[ij|rs] represents the plurality of intermediate equations;

$[i^T j^T |k^T l^T]$ represents the plurality of relativistic integrals;

$\Gamma_{kr}^{T(1)\dagger}$, $\Gamma_{sl}^{T(1)}$, $\Gamma_{kr}^{T(0)\dagger}$ and $\Gamma_{sl}^{T(0)}$ each represent transformation matrices; and N represents a number of Cartesian basis functions.

5. The method of claim 4 wherein said inputting step includes inputting said non-relativistic physical description including the names of the atoms therein, the electron configurations of said atoms and the bonding configurations between said atoms in said predetermined molecular structure, said evaluating step includes characterizing the expected response of said predetermined molecular structure in catalytic reactions, said evaluating step further comprising constructing a potential energy data set depicting a relativistic potential energy surface configuration for said predetermined molecular structure, and said generating said relativistic physical description step includes generating, as said at least one of said relativistic features, a relativistic equilibrium geometry descriptive of said predetermined molecular structure.

6. The method of claim 5 wherein said generating said relativistic physical description step further comprises generating, as said at least one of said relativistic features, a bond configuration including bond lengths between atoms contained in said predetermined molecular structure.

7. The method of claim 5 wherein said generating said relativistic physical description step further comprises generating a description of the equilibrium bond length occurring at a minimum of said relativistic potential energy surface configuration.

8. A computer system for generating and displaying a relativistic physical description of a predetermined molecular structure containing heavy elements having relativistic features, said computer system comprising:

input means for inputting a non-relativistic physical description of said predetermined molecular structure;

memory means for storing a first data set comprising non-relativistic, Cartesian, two-electron repulsion integrals;

transformation means for transforming said first data set into a second data set, said second data set comprising relativistic integrals;

means for processing said relativistic integrals to generate relativistic numerical parameters of said predetermined molecular structure;

evaluation means for classifying said relativistic numerical parameters and said non-relativistic physical description;

description means, responsive to said evaluation means, for generating said relativistic physical description of said predetermined molecular structure, said description means generating a specification of at least one of said relativistic features of said predetermined molecular structure; and display means for displaying said relativistic physical description of said predetermined molecular structure.

9. The system of claim 8 wherein said transformation means includes means for transforming said first data set into an intermediate data set comprising intermediate integrals functionally related to said non-relativistic, Cartesian, two-electron repulsion integrals, and for transforming said intermediate data set into said second data set.

10. The system of claim 9 wherein said transformation means comprises means for evaluating the following expression:

$$[i^T j^T |rs] = \sum_{p=1}^{N} \sum_{q=1}^{N} \{\Gamma_{ip}^{T(1)\dagger}[pq|rs]\Gamma_{qj}^{T(1)} + \Gamma_{ip}^{T(0)\dagger}[pq|rs]\Gamma_{qj}^{T(0)}\}$$

where:

[pq|rs] is a bracket notation representing the plurality of two-electron repulsion integrals;

$[i^T j^T |rs]$ represents the plurality of intermediate set of integrals;

$\Gamma_{ip}^{T(1)\dagger}$, $\Gamma_{qj}^{T(1)}$, $\Gamma_{ip}^{T(0)\dagger}$, and $\Gamma_{qj}^{T(0)}$ each represent transformation matrices; and N represents a number of Cartesian basis functions.

11. The system of claim 10 wherein said transformation means further includes means for evaluating the following expression:

$$[i^T j^T |k^T l^T] = \sum_{p=1}^{N} \sum_{q=1}^{N} \{\Gamma_{kr}^{T(1)\dagger}[ij|rs]\Gamma_{sl}^{T(1)} + \Gamma_{kr}^{T(0)\dagger}[ij|rs]\Gamma_{sl}^{T(0)}\}$$

where:

[ij|rs] represents the plurality of intermediate equations;

$[i^T j^T |k^T l^T]$ represents the plurality of relativistic integrals;

$\Gamma_{kr}^{T(1)\dagger}$, $\Gamma_{sl}^{T(1)}$, $\Gamma_{kr}^{T(0)\dagger}$ and $\Gamma_{sl}^{T(0)}$ each represent transformation matrices; and N represents a number of Cartesian basis functions.

12. The system of claim 11 wherein said input means further includes means for inputting the names of the atoms in said predetermined molecular structure, the electron configurations of said atoms and the bonding configurations between said atoms, said evaluation means further includes means for characterizing the expected response of said predetermined molecular structure in catalytic reactions and constructing a potential energy data set depicting a relativistic potential energy surface configuration for said predetermined molecular structure, and said description means further includes means for generating a relativistic equilibrium geometry descriptive of said predetermined molecular structure.

13. The system of claim 12 wherein said description means further includes means for generating a bond configuration including bond lengths between atoms contained in said predetermined molecular structure.

14. The system of claim 13 wherein said description means further includes means for generating a description of the equilibrium bond length occurring at a minimum of said relativistic potential energy surface configuration.

* * * * *